United States Patent [19]

Sasahara

[11] Patent Number: 5,335,173
[45] Date of Patent: Aug. 2, 1994

[54] MEDICAL DIAGNOSIS IMAGE DISPLAY METHOD AND APPARATUS

[75] Inventor: Osamu Sasahara, Kashiwa, Japan

[73] Assignee: Hitachi Medical Corp., Tokyo, Japan

[21] Appl. No.: 925,773

[22] Filed: Aug. 7, 1992

[30] Foreign Application Priority Data

Aug. 8, 1991 [JP] Japan .................................. 3-199049

[51] Int. Cl.$^5$ ............................................. G06F 15/00
[52] U.S. Cl. ............................ 364/413.22; 364/413.19
[58] Field of Search ...................... 364/413.13, 413.14, 364/364.19, 413.22; 395/124; 340/729

[56] References Cited

U.S. PATENT DOCUMENTS

| 4,866,612 | 9/1989 | Takagi ............................ 364/413.22 |
| 5,166,875 | 11/1992 | Machida ......................... 364/413.13 |
| 5,170,347 | 12/1992 | Tuy et al. ....................... 364/413.19 |

Primary Examiner—Roy N. Envall, Jr.
Assistant Examiner—Khai Tran
Attorney, Agent, or Firm—Antonelli, Terry, Stout & Kraus

[57] ABSTRACT

A medical diagnosis image display method comprising the steps of transforming respective three-dimensional image information on a skull of a subject patient to be examined and diagnosed and skin covering the outer surface of the skull; obtaining respective two-dimensional image information on the respective three-dimensional images of the skull and skin viewed according to the same viewing perspective and storing the two-dimensional image information in a memory; displaying one item of the two-dimensional image information, for example, the two-dimensional image of the skull, and designating part of the displayed image information to be cut out, and automatically reading out the corresponding skin image information of the area corresponding to the designated cut out part; and displaying the read out skin image information in the cut out part of the image of the skull already displayed.

6 Claims, 13 Drawing Sheets

MEDICAL DIAGNOSIS IMAGE DISPLAY METHOD AND APPARATUS

BACKGROUND OF THE INVENTION

The present invention relates to medical diagnosis image display methods and apparatuses, and more particularly to a medical diagnosis image display method and apparatus for rotating in a three-dimensional plane an image displayed on a monitor and imaging the rotated image.

A medical diagnosis display apparatus of this type is very advantageous for diagnosis because, for example, a head, or other body part, of a subject patient to be examined and diagnosed can be viewed in various directions.

The rotating function is incorporated into a medical diagnosis image display apparatus for obtaining a tomogram image of a subject to be diagnosed such as an X-ray computed tomography (XCT), a magnetic resonance image diagnosis device (MRI) or a single photon emission CT (SPECT).

Figure 7A:
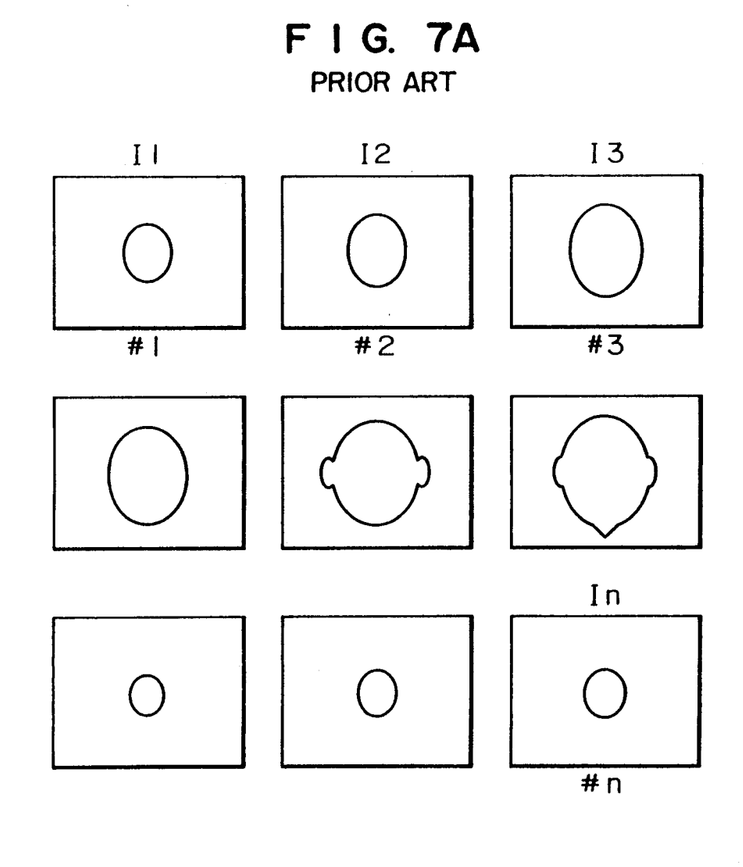
FIGS. 7A-7B illustrate a method of forming 3-dimensional image information.
Figure 7B:
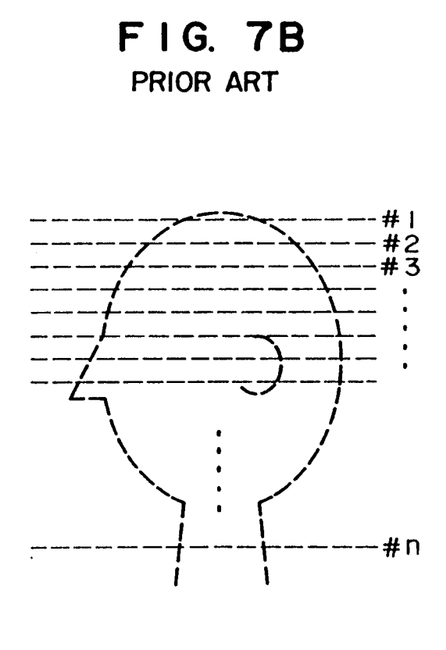

One conventional method of three-dimensionally rotating an image displayed on a monitor and displaying an image obtained in the course of image rotation is as follows:

For example, sliced images are obtained as $I_1, I_2, I_3, \ldots, I_n$ by slicing an image of a head of a subject to be examined and diagnosed, transversely to the longitudinal body axis direction, as shown in FIG. 7A. The two-dimensional image information on the respective sliced images $I_1, I_2, I_3, \ldots, I_n$ is obtained to provide the three-dimensional image information corresponding to the sliced positions of the subject, as shown in FIG. 7B.

On the basis of the three-dimensional image information thus obtained, angle designation information, for example, from a track ball is used to provide two-dimensional image information viewed in the direction of the designated angle and an image is displayed on the basis of the two-dimensional image information.

In this case, if the viewing angle is changed linearly by the track ball, the image displayed on the monitor is rotated three-dimensionally.

As described above, since the two-dimensional image displayed on the monitor can be viewed in various directions, this method is very convenient for examination, for example, of a soft tissue or a bone tissue of a subject.

However, conventional devices would display these soft tissue and bone tissue separately without allowing for the positional relationship between them, that is none of the conventional devices display the soft tissue and bone tissues together in the relationship thereinbetween.

Thus, for example, if an operation is performed on the head of a burn patient, the positional relationship of the soft tissue to the skull is not immediately or accurately recognized thereby prohibiting the necessary operation procedures from being immediately determined.

SUMMARY OF THE INVENTION

It is therefore an object of the present invention to provide a medical examination and diagnosis image display method and apparatus for accurately recognizing a positional relationship between soft tissue and bone tissue.

In order to achieve the above object, the present invention provides a medical examination and diagnosis image display apparatus comprising:

a first memory for storing three-dimensional image information only regarding soft tissue of a subject patient to be examined and diagnosed;

a second memory for storing three-dimensional image information only regarding bone tissue of the subject patient;

operation circuits for transforming the respective three-dimensional image information stored in said first and second memories into corresponding two-dimensional image information to be viewed from a same viewing perspective;

a third and a fourth memory for storing respective two-dimensional image information transformed by the respective operation circuits;

a display for displaying as base information, the two-dimensional information items stored in the third and fourth memories;

a region designating unit for designating a part of the image displayed on the display; and an image information replacing circuit for replacing the image information being displayed thus far with image information corresponding to a part of the image designated by the region designating unit, the image information having not been displayed as the base image or stored in the third and fourth memories.

For example, when the soft tissue of the subject patient is displayed on the display, the medical diagnosis image apparatus transforms three-dimensional image information in the first memory to two-dimensional image information using an operation circuit and displays the two-dimensional information on the display via the third memory.

When the three-dimensional image information is transformed into to two-dimensional image information, the two-dimensional image information comprises information obtained by viewing the three-dimensional image information from any viewing perspective.

At the same time, the three-dimensional image information regarding the bone tissue from the second memory is transformed by the other operation circuit into two-dimensional image information, which is stored in the fourth memory.

The two-dimensional information in this case is comprises information obtained by viewing the three-dimensional image information from exactly the same viewing perspective as the two-dimensional image information of the soft tissue is viewed.

When a part of the image region of the soft tissue displayed on the display is designated by the region designating unit, the image information replacing circuit reads out of the fourth memory the image of the bone tissue in the designated region part in place of the soft tissue image of the designated region part and displays the read-out image.

Thus, as will be obvious from this operation, the positional relationship of the soft tissue to the bone tissue is clearly recognized.

Therefore, if an operation is performed on the head of a burn patient, the necessary procedures for operating can accurately be determined, since the positional relationship between the skull and the soft tissue on the outer surface of the skull is accurately determined.

DESCRIPTION OF THE PREFERRED EMBODIMENTS

Figure 1:
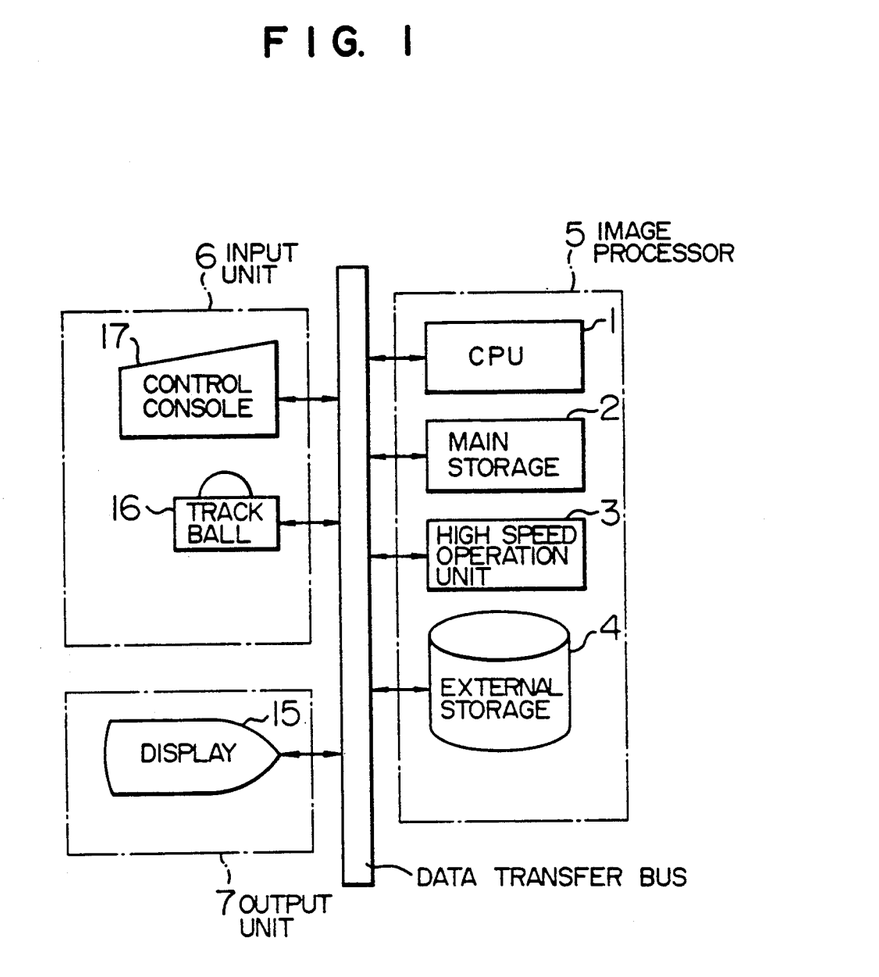
FIG. 1 is a schematic diagram of a medical examination and diagnosis image display of the present invention.

FIG. 1 is a schematic diagram of the inventive medical diagnosis image display. An image processor 5 includes a CPU 1, a main storage 2, a high speed operation unit 3, and an external storage 4.

An input unit 6 includes a control console 17, and track ball 16.

An output unit 7 includes a display 15. The respective units are connected to a data transfer bus.

Figure 2:
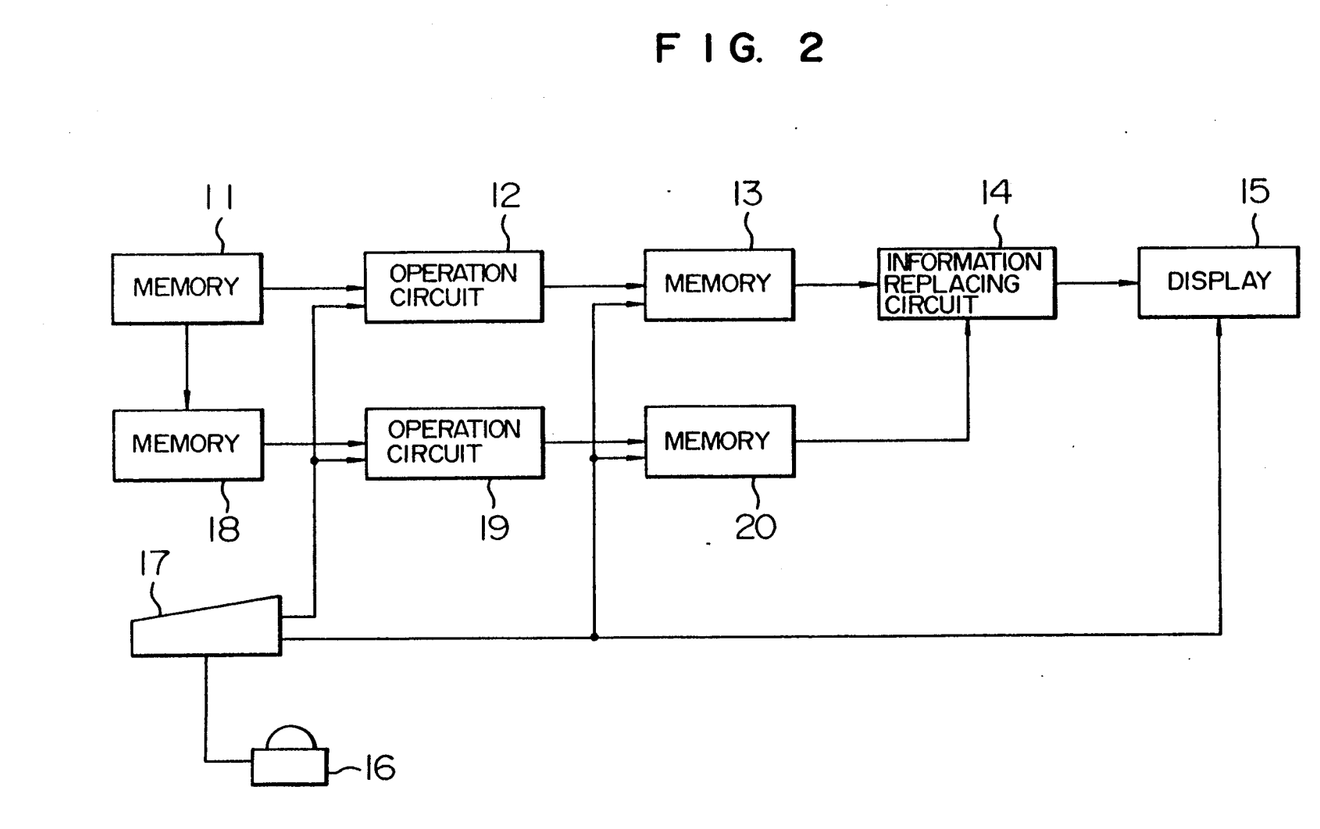
FIG. 2 is a block diagram indicative of image processing according to the present invention.

FIG. 2 is a block diagram indicative of image processing according to the present invention.

In FIG. 2, a three-dimensional image is constructed by superposing sliced images of soft tissue (skin) of the head of a subject patient to be examined and diagnosed, as shown in FIGS. 7A and 7B, and the resulting image information is stored in memory 11.

The three-dimensional image information which is the output of memory 11 is converted to two-dimensional image information by the operation circuit 12, which first forms two-dimensional image information of an obtained by viewing the front of the patient's head and stores the resulting two-dimensional image information into the memory 13.

The two-dimensional image information stored in the memory 13 is displayed on the display 15 through an information replacing circuit 14 to be described later in more detail.

An operator can operate the track ball 16 while viewing the display 15, so that the two-dimensional image information displayed on the display 15 can be rotated by operating the track ball 16. A signal deriving from the operation of the track ball 16 is input to the operation circuit 12 via the control console 17. The coordinate axes for the three-dimensional image information are angle transformed in accordance with the input signal to thereby constitute two-dimensional image information viewed in any direction, and the two-dimensional image information is stored in the memory 13.

A memory 18 is provided to store three-dimensional image information of the skull of the subject patient. The three-dimensional image information is input to the operation circuit 19, which then converts the image information to two-dimensional image information. The two-dimensional image information in this case comprises information obtained by viewing the three-dimensional image of the skull from exactly the same viewing perspective as the three-dimensional image is viewed when the operation circuit 12 constitutes the two-dimensional image information of the soft tissue.

The two-dimensional image information thus constituted is stored in the memory 20.

The control console 17 is capable of designating a specific part region of the soft tissue of the head displayed on the display 15. For example, any particular region can be designated by moving a cursor on the screen of the display 15.

At this time, the information replacing circuit 14 replaces the image of the soft tissue in the designated region with the image of the skull in the memory 20 corresponding to the designated region to display the new image.

The operation of this apparatus will be described hereinafter.

OPERATION 1

Figure 3A:
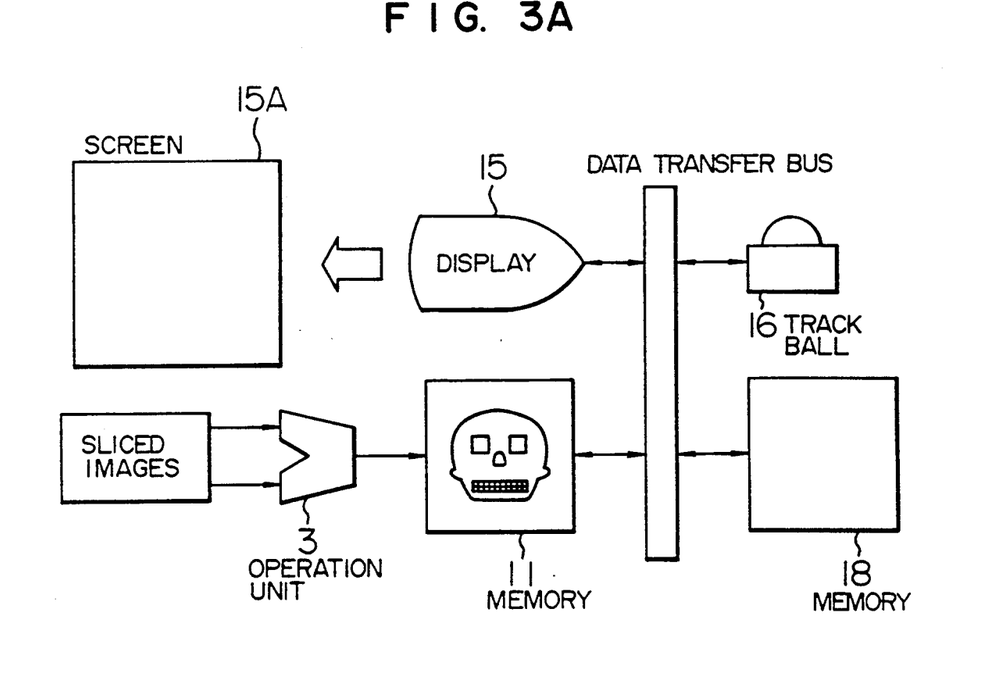
FIGS. 3A-3H illustrate the display operation of the image display according to the present invention.

Insertion of the Image of Skull Tissue into the Corresponding Image of the Soft Tissue First, as shown in FIG. 3A, the operation unit 3 creates three-dimensional image information from the information on the sliced images of the skull of a subject, as shown in FIG. 7A and stores the three-dimensional image information temporarily in the memory 11.

Figure 3B:
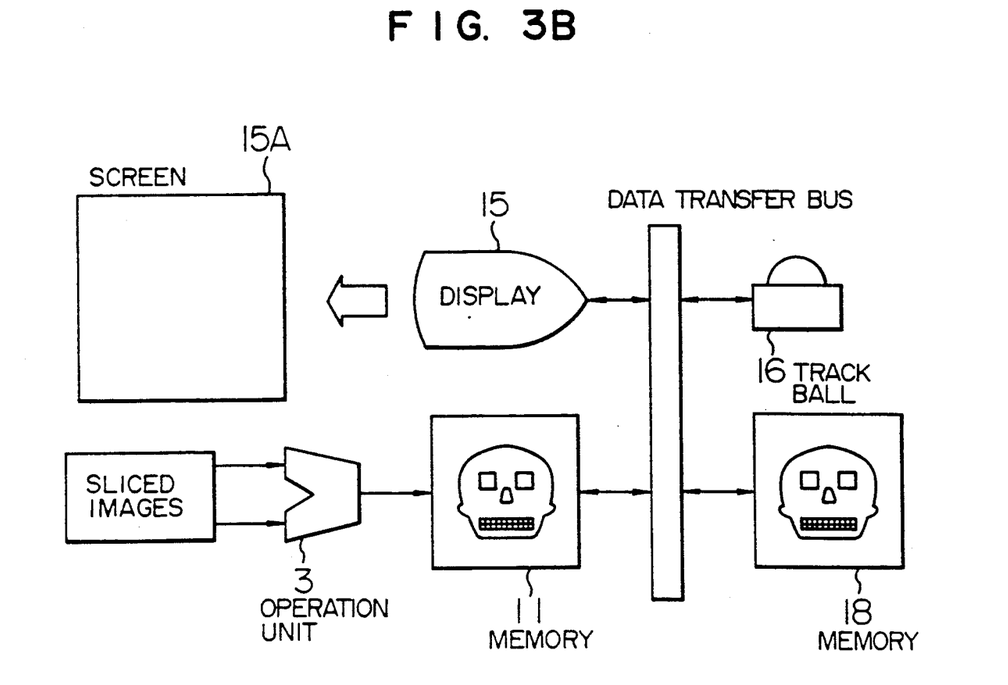

FIG. 3B shows that the information stored in the memory 11 is stored in the memory 18.

Figure 3C:
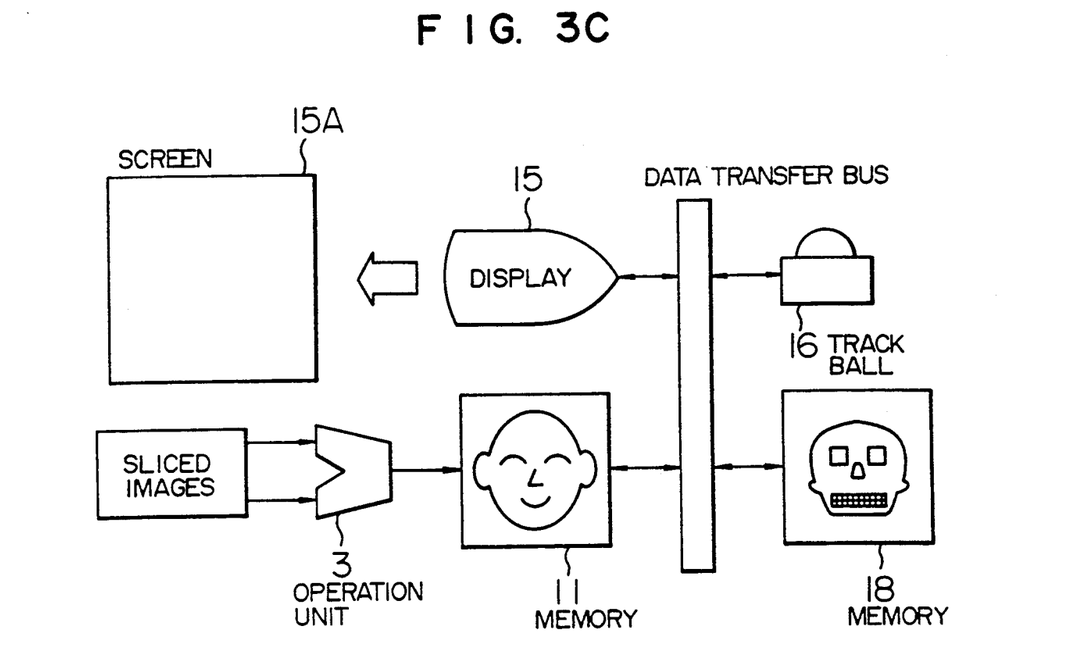

As shown in FIG. 3C, the operation unit 3 creates three-dimensional image information of the skin or soft tissue of the subject patient from the information on the sliced images shown in FIG. 7A and stores the three-dimensional information in the memory 11. At this time, the three-dimensional image information of the skull stored so far in the memory 11 is overwritten.

Figure 3D:
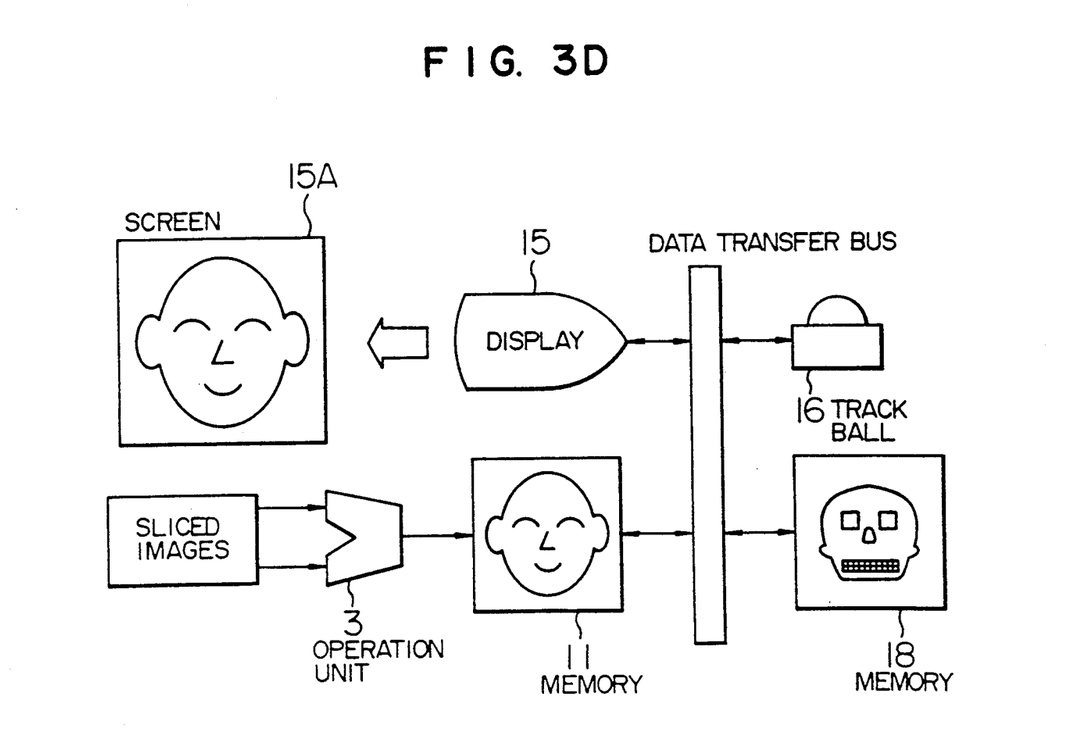

As shown in FIG. 3D, the operation circuit 12 shown in FIG. 2 converts the three-dimensional image information on the soft tissue stored in the memory 11 to two-dimensional image information, which is displayed on the screen 15A of the display 15.

At this time, the two-dimensional image information is obtained as the three-dimensional image information rotated to any angle by the track ball 16.

Figure 3E:
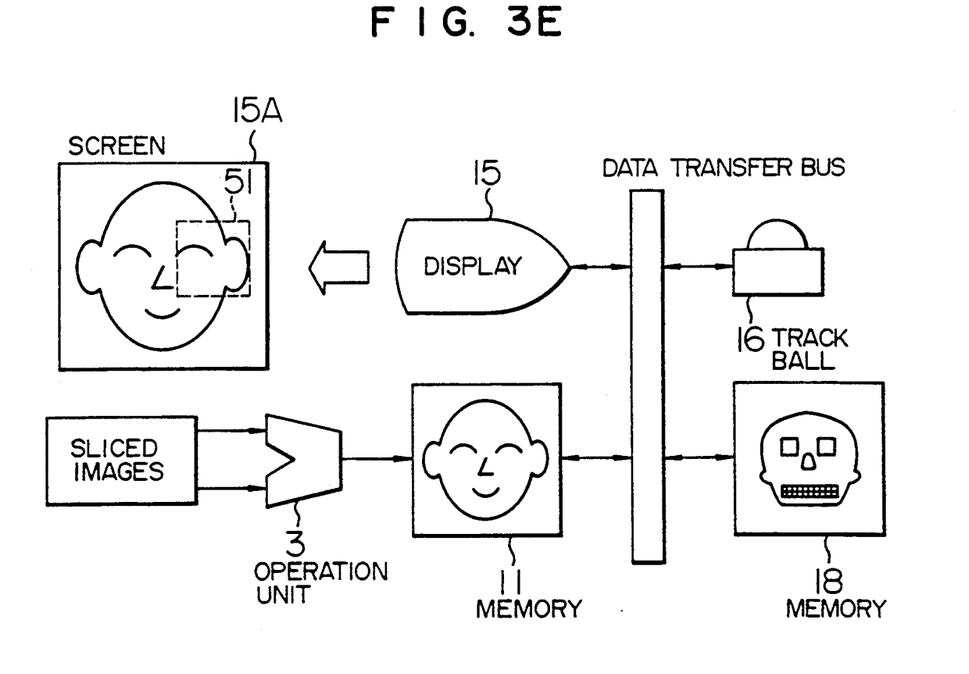

As shown in FIG. 3E, the control console 17 shown in FIG. 1 designates any desired part 51 of the screen region 15A of the display 15.

Figure 3F:
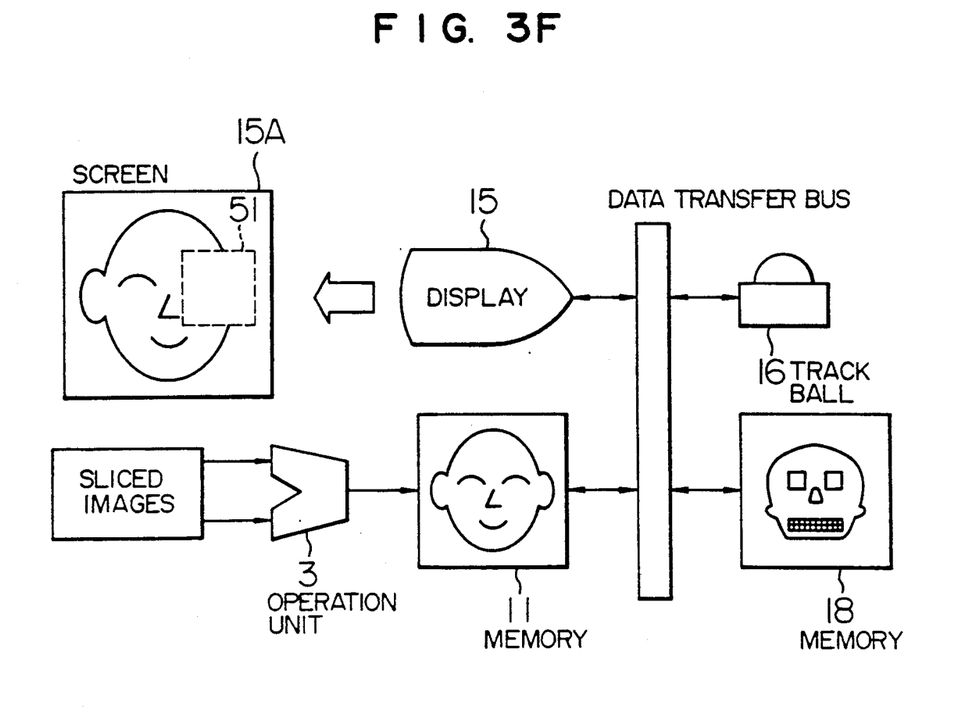

As shown in FIG. 3F, the image information on the designated part 51 of the screen region 15A is then erased.

Figure 3G:
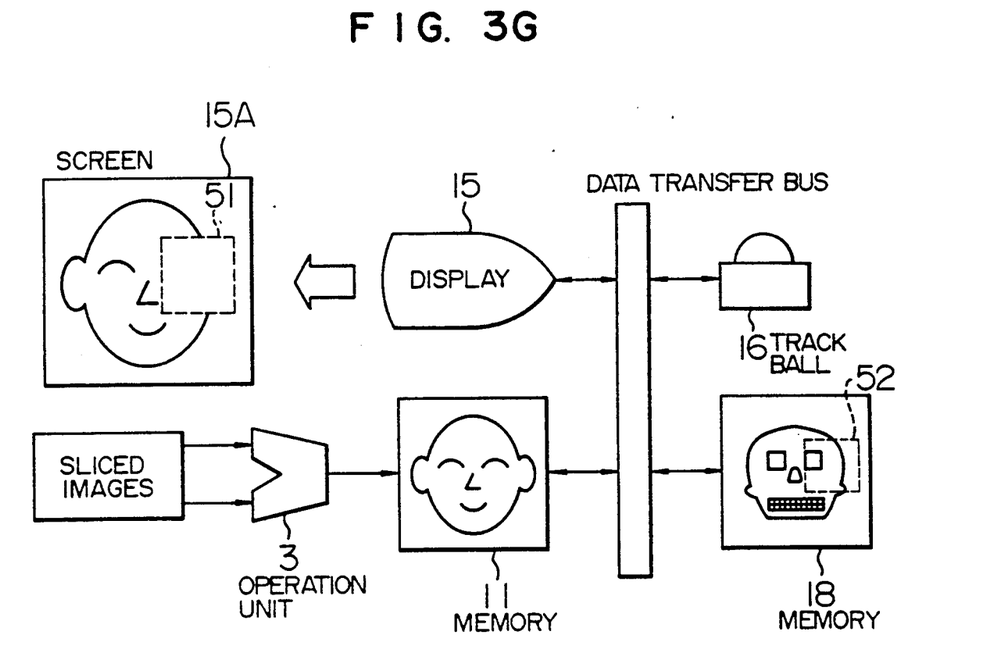

As shown in FIG. 3G, image information on an area 52 corresponding to the designated part 51 of the screen region 15A is read out of the skull memory 18.

Figure 3H:
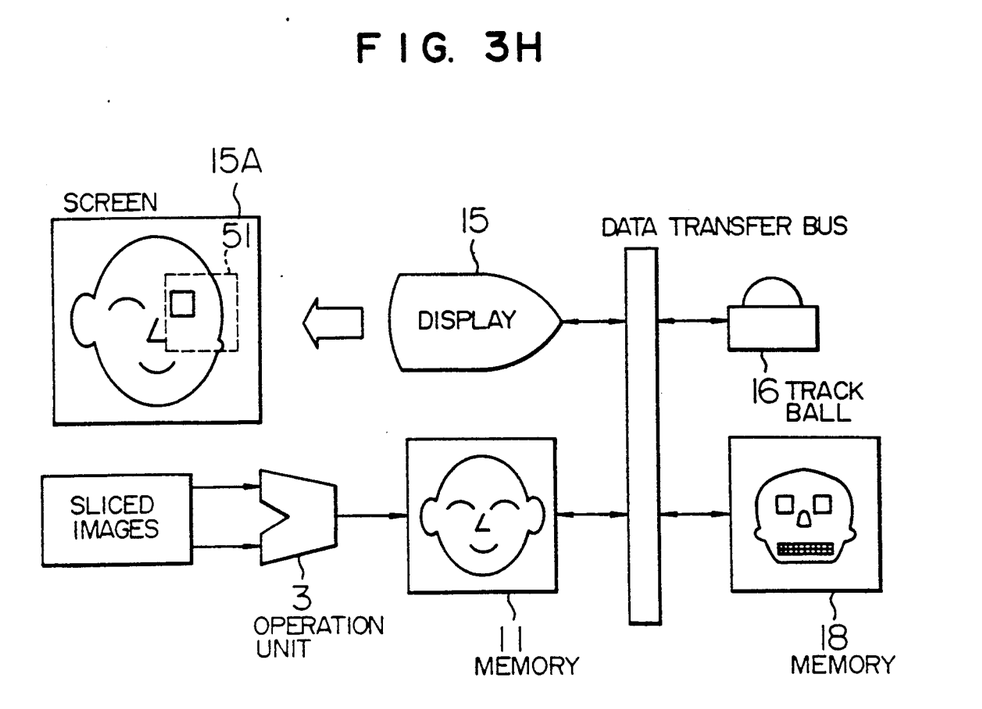

As shown in FIG. 3H, the image information read out of the memory 18 is displayed on the screen region 15A.

Figure 4:
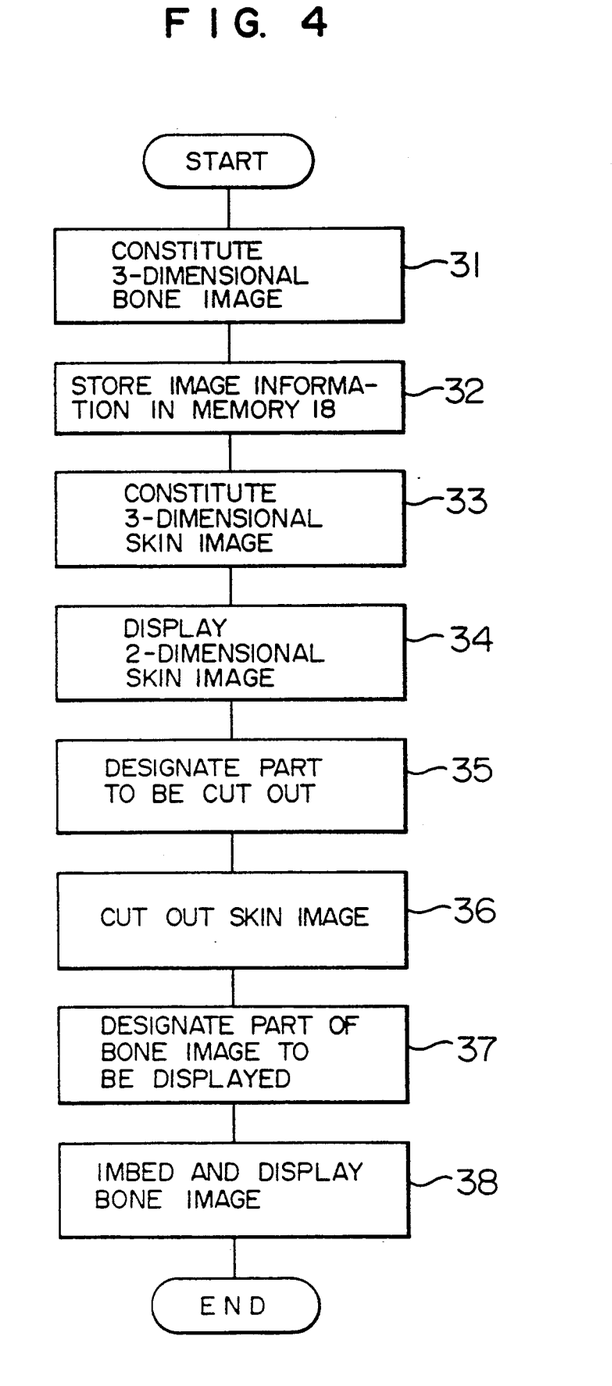
FIG. 4 is a flowchart indicative of the operation of the image display apparatus according to the present invention directed to FIGS. 3A-3H.

FIG. 4 is a flowchart indicative of the operation set forth above.

First, a three-dimensional image on the skull is constituted in the memory 11 (step 31) and the information on the image is stored in the memory 18 (step 32). A three-dimensional image of the skin is constituted in the memory 11 (step 33) and is then transformed into a two-dimensional image, which is then displayed on the display screen region 15A (step 34). An operator designates a part 51 of the skin two-dimensional image to be cut out, as shogun in FIG. 3G (step 35). Thus, the skin image is automatically cut out (step 36) and the corresponding part 52 of the bone image to be displayed is automatically designated (step 37), as shown in FIG. 3G. The bone image is then imbedded into the place where the skin image is cut out and displayed as shown by 15A in FIG. 3H (step 38).

OPERATION 2

Insertion of the Image of the Soft Issue into the Image of the Bone Concerned

Figure 5A:
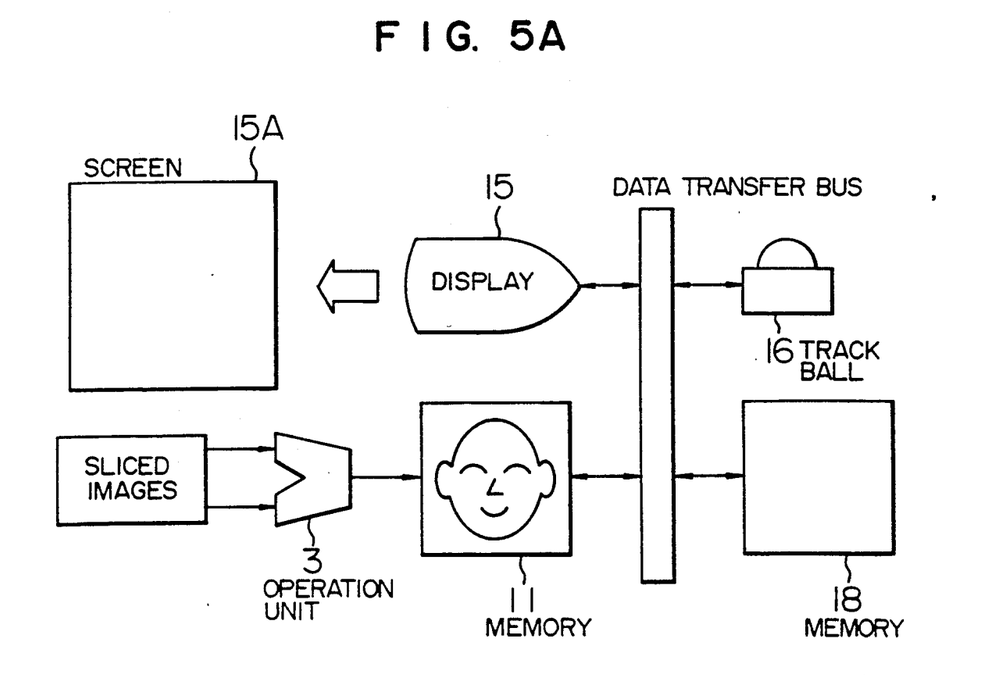
FIGS. 5A-5H illustrate another display operation of the inventive display.

First, as shown in FIG. 5A, the operation unit 3 creates three-dimensional image information from the information on the sliced images of the skin of a subject patient, as shown in FIG. 7A and stores the three-dimensional image information temporarily in the memory 11.

Figure 5B:
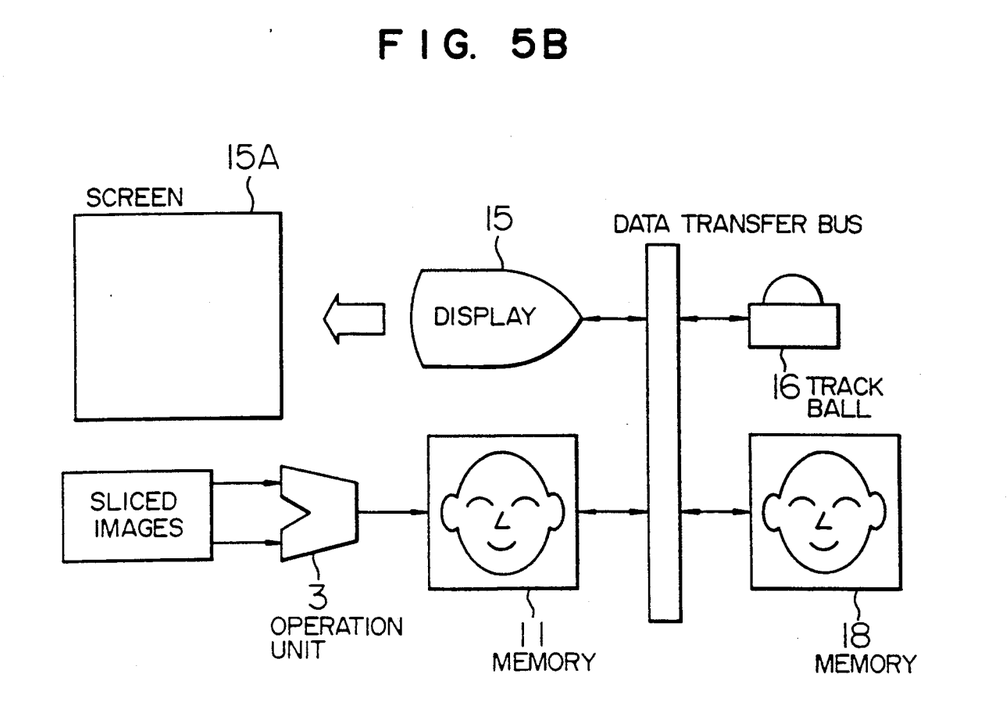

FIG. 5B shows that the information stored in the memory 11 is also stored in the memory 18.

Figure 5C:
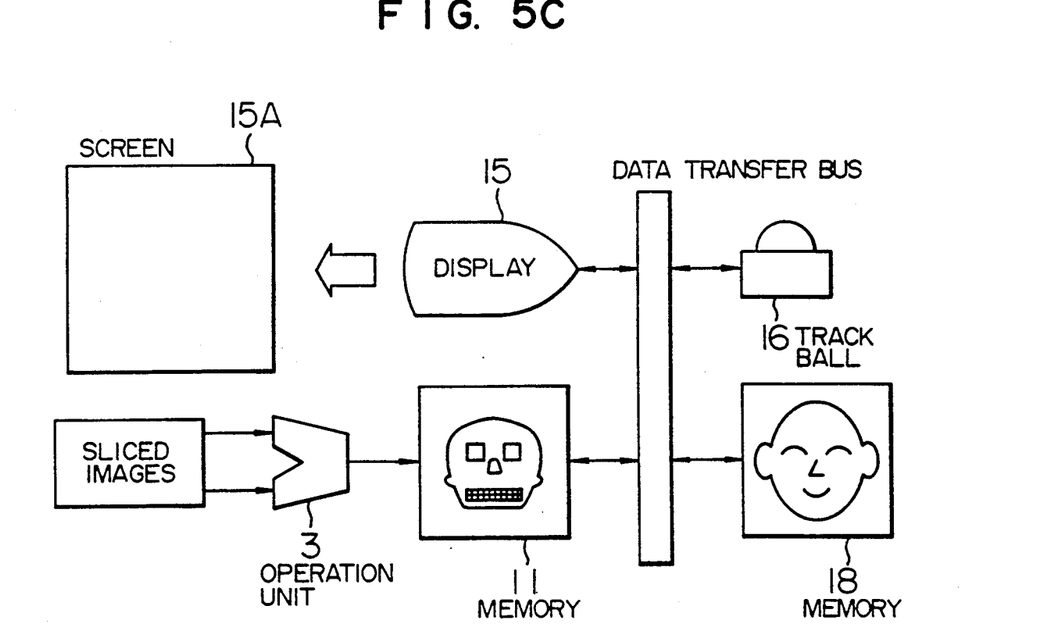

As shown in FIG. 5C, the operation unit 3 creates three-dimensional image information of the skull of the subject patient from the information on the sliced images shown in FIG. 7A and stores the three-dimensional information in the memory 11. At this time, the three-dimensional image information of the skin stored so far in the memory 11 is overwritten.

Figure 5D:
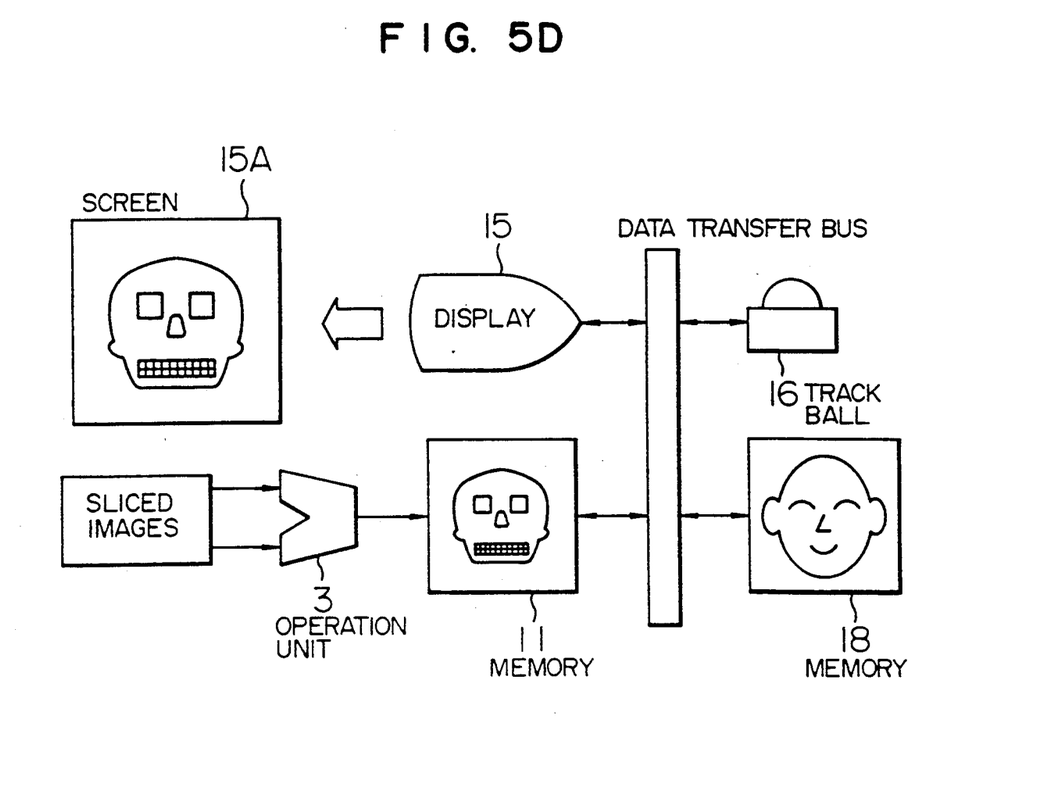

As shown in FIG. 5D, the operation circuit 12 shown in FIG. 2 converts the three-dimensional image information of the skull stored in the memory 11 to two-dimensional image information, which is displayed on the screen region 15A of the display 15.

At this time, the two-dimensional image information is obtained as the three-dimensional image information rotated to any angle by the track ball 16.

Figure 5E:
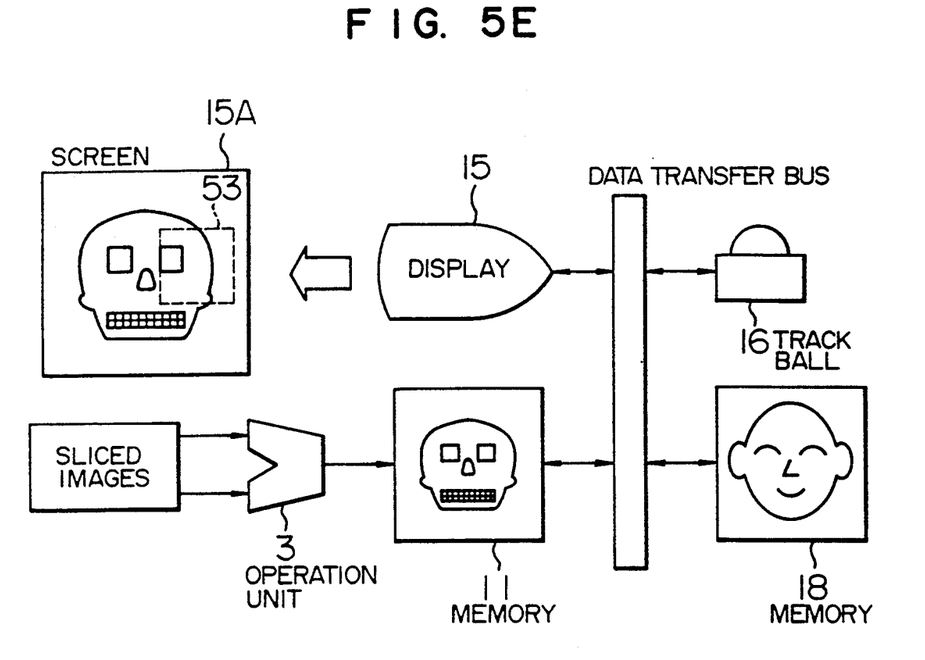

As shown in FIG. 5E, the control console 17 shown in FIG. 1 designates any desired part 53 of the screen region 15A of the display 15.

Figure 5F:
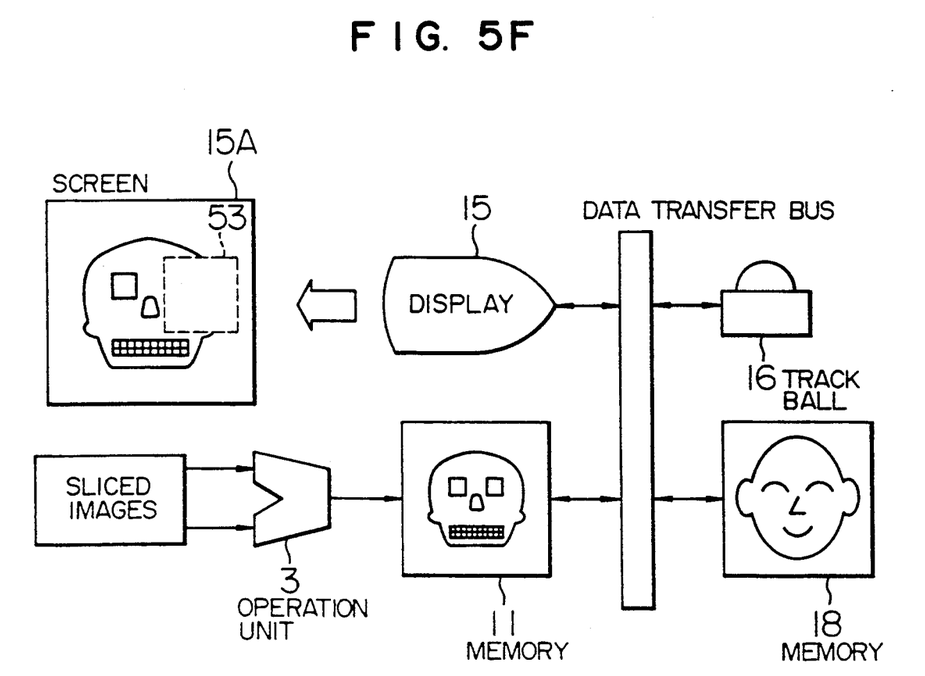

As shown in FIG. 5F, the image information on the designated part 53 of the screen region 15A is then overwritten.

Figure 5G:
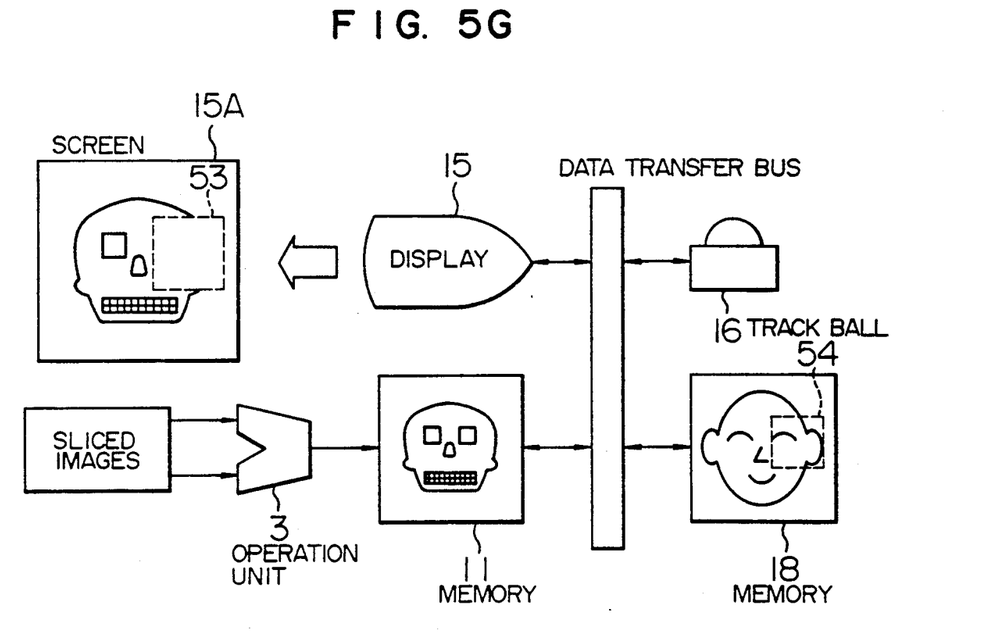

As shown in FIG. 5G, image information on an area 54 corresponding to the designated part 53 of the screen region 15A is read out of the memory 18 which stores three-dimensional skin image information.

Figure 5H:
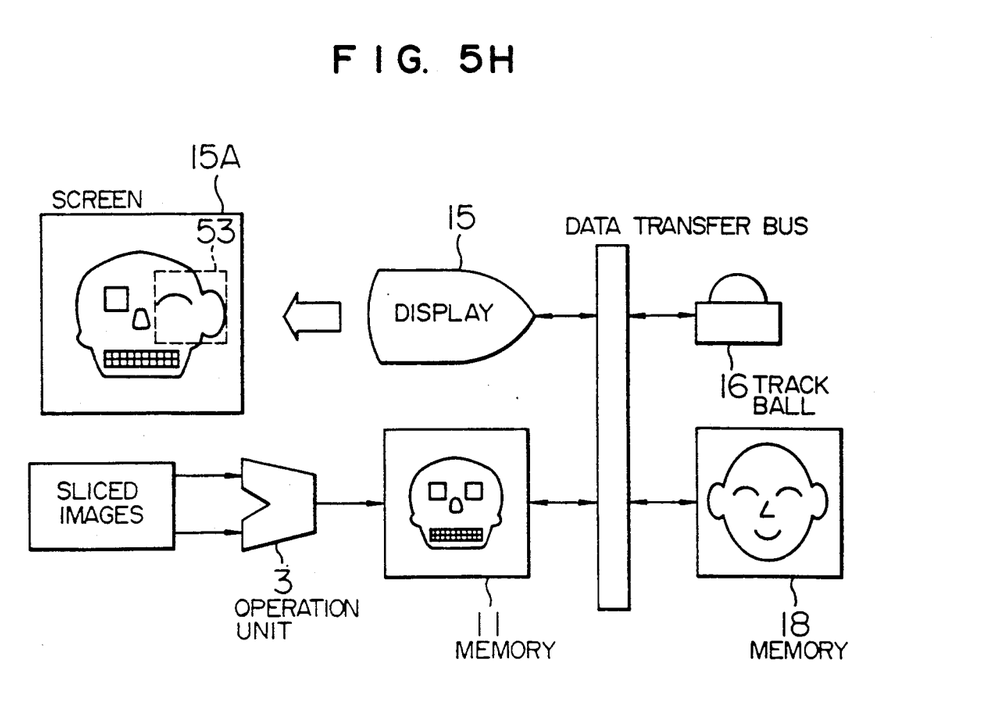

As shown in FIG. 5H, the image information read out of the memory 18 is displayed on the screen region 15A.

Figure 6:
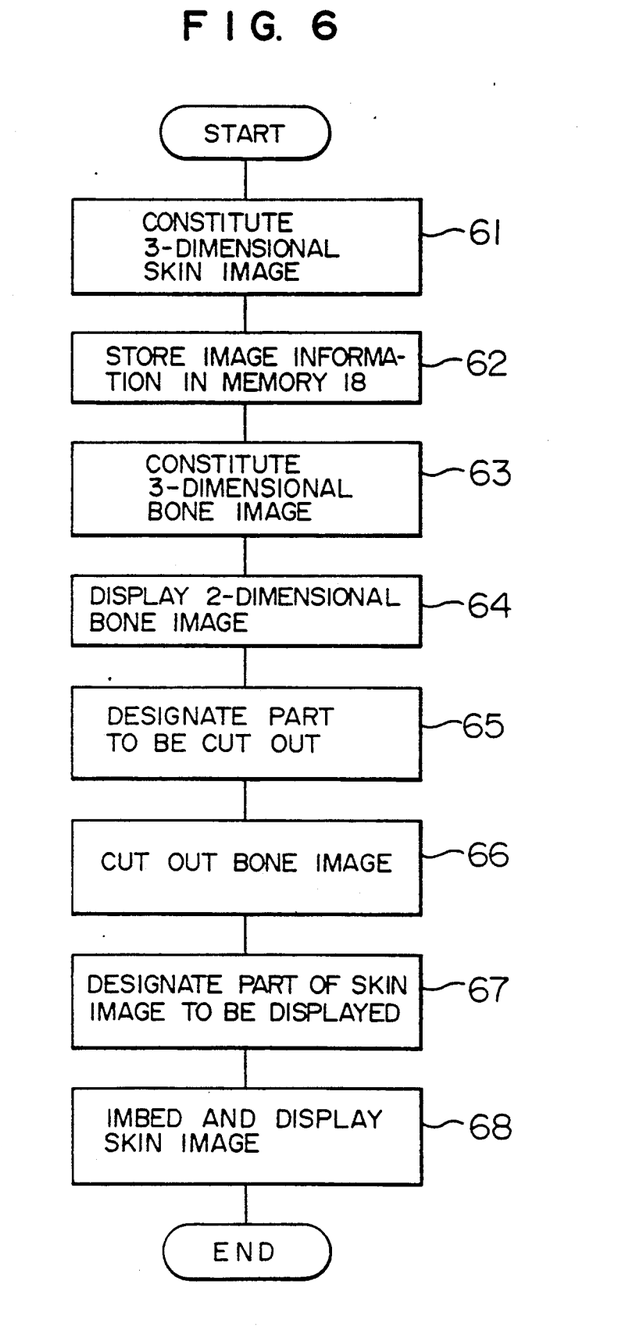
FIG. 6 is a flowchart indicative of the display operation of the display of FIGS. 5A-5H.

FIG. 6 is a flowchart indicative of the above operation set forth above.

First, a three-dimensional skin image is constituted in the memory 11 (step 61) and the information on the image is stored in the memory 18 (step 62). A three-dimensional image of the bone is constituted in the memory 11 (step 63) and is then transformed into a two-dimensional image, which is then displayed on the screen region 15A (step 64). An operator designates a part 53 of the bone two-dimensional image to be cut out, as shown in FIG. 5E (step 65). Thus, the bone image is automatically cut out (step 66) and the corresponding part 54 of the skin image to be displayed is automatically designated (step 67), as shown in FIG. 5G. The skin image is then imbedded into the place where the bone image is cut out and displayed as shown by the screen region 15A in FIG. 5H (step 68).

As will be obvious from the two illustrative examples of the operations, the positional relationship between the skull and soft tissues (skin) is clearly understood.

While in the embodiment the examples of the skull and soft tissues are taken, the present invention is applicable to soft tissues different in kind.

I claim:

1. A medical examination and diagnosis image display method, said method comprising the steps of:

transforming three-dimensional image information of a first tissue of a subject patient to be examined and diagnosed into a first two-dimensional projected image information viewed from a first viewing perspective and displaying the two-dimensional projected image information, said first two-dimensional projected image information being obtained by performing a projection operation on the three-dimensional image information of the first tissue;

transforming three-dimensional image information of a second tissue of the subject patient into a second two-dimensional projected image information viewed from the first viewing perspective and storing the second two-dimensional projected image information in a first memory, said second two-dimensional projected image information being obtained by performing a projection operation on the three-dimensional image information of the second tissue;

designating a part of the first two-dimensional projected image of the first tissue to be cut out from the displayed first two-dimensional projected image;

reading out image information of the second tissue corresponding to the designated part from the first memory;

integrating image information of the second tissue read out from the first memory into the part designated of the first two-dimensional projected image of the first tissue; and displaying the integrated image.

2. A medical examination and diagnosis image display method according to claim 1, wherein the first tissue is a bone tissue while the second tissue is a soft tissue on the outer surface of the bone tissue.

3. A medical examination and diagnosis image display method according to claim 1, wherein the first tissue is a soft tissue while the second tissue is a bone tissue on the inside surface of the soft tissue.

4. A medical examination and diagnosis image display apparatus comprising:

a first memory for storing three-dimensional image information of a first tissue of a subject patient to be examined and diagnosed;

a second memory for storing three-dimensional image information of a second tissue of the subject patient;

operation means for transforming respective three-dimensional image information stored in said first and second memories into corresponding two-dimensional image information viewed according to the same viewing perspectives by performing a projection operation on the three-dimensional image information;

a third memory for storing the two-dimensional image information of the first tissue transformed by said operation means;

a fourth memory for storing two-dimensional image information of the second tissue transformed by said operation means;

display means for displaying the image information stored in said third memory;

designating means for designating part of the image displayed on said displaying means; and imaging means for reading out of said fourth memory image information corresponding to the image part designated by said designating means and displaying the read-out image information in the place of the designated part of the displayed image.

5. A medical examination and diagnosis image display apparatus according to claim 4, wherein the first tissue is a bone tissue while the second tissue is a soft tissue on the outer surface of the bone.

6. A medical examination and diagnosis image display apparatus according to claim 4, wherein the first tissue is a soft tissue while the second tissue is a bone tissue on the inside surface of the soft tissue.

* * * * *